Figure 1:
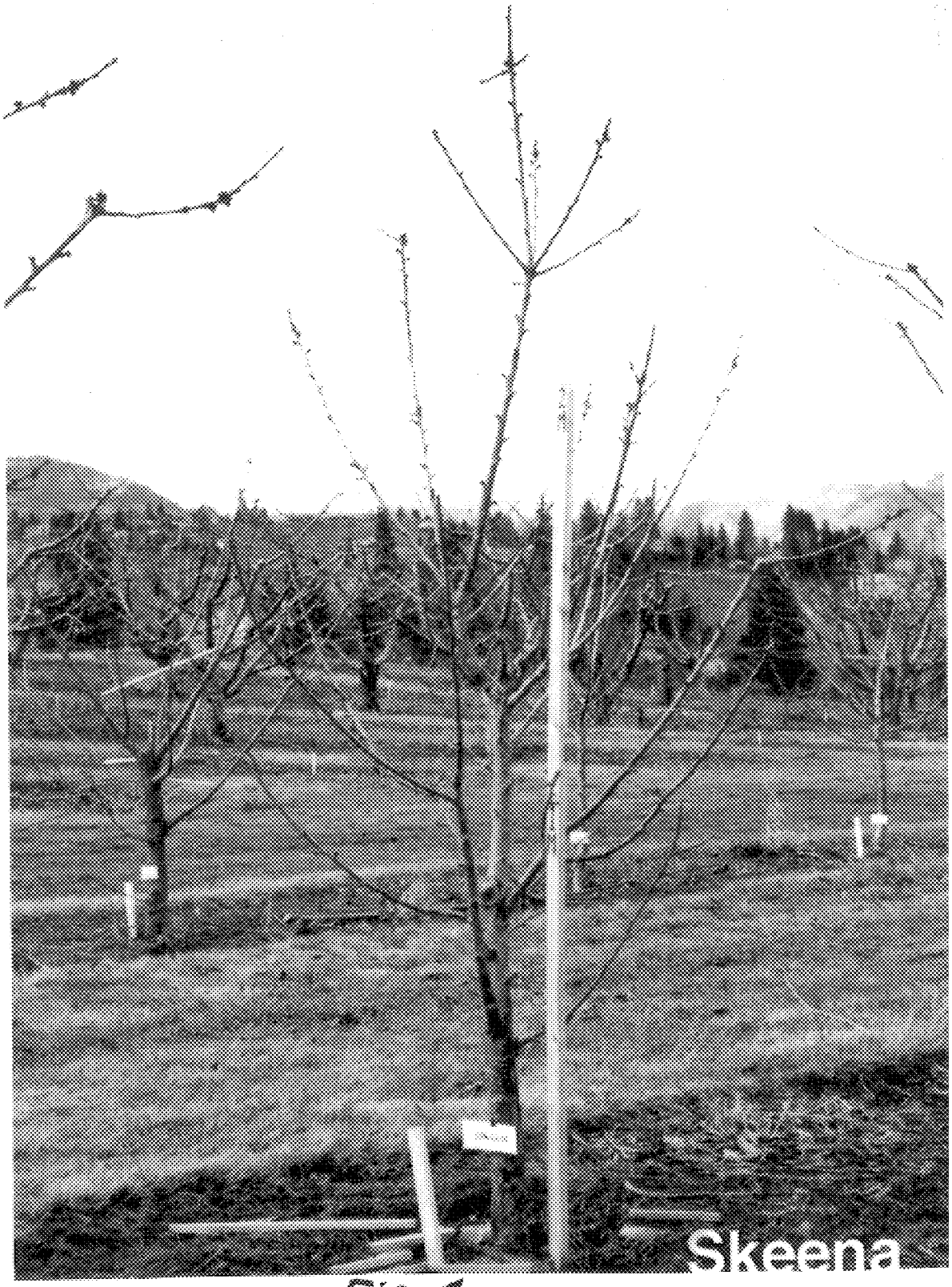

US00PP11392P

United States Patent [19]

Lane

[11] Patent Number: Plant 11,392

[45] Date of Patent: May 30, 2000

[54] CHERRY TREE NAMED 'SKEENA'

[75] Inventor: W. David Lane, Summerland, Canada

[73] Assignee: Okanagan Plant Improvement Co. Ltd., Summerland, Canada

[21] Appl. No.: 09/104,413

[22] Filed: Jun. 25, 1998

[51] Int. Cl.[7] ..... A01H 5/00

[52] U.S. Cl. ..... Plt./181

[58] Field of Search ..... Plt./181

[56] References Cited

U.S. PATENT DOCUMENTS

P.P. 5,478 5/1985 Anderson et al. ..... Plt./181
P.P. 8,051 12/1992 Toyama ..... Plt./181

*Primary Examiner*—Howard J. Locker
*Assistant Examiner*—Wendy A Baker

[57] ABSTRACT

A new and distinct variety of cherry tree, originating from a controlled cross of the seed parent '2N-60-7' and the pollen parent '2N-38-32', is described. Under growing conditions at the Pacific Agri-Food Research Centre (PARC) Summerland located at Summerland in the Okanagan Valley of British Columbia, Canada the variety is distinguished by its large kidney shaped fruit, with glossy, wine red to mahogany colored skin with fine light dots, and red to dark red flesh. The fruit has a non-prominent suture and a flat to slightly hollow apex and is borne on medium-long, thick stems. The stone of the fruit is round, is large relative to the fruit, and has an undeveloped keel. The fruit matures late in the cherry season, 12 to 16 days after 'Van' and 'Bing' and 1 to 5 days after 'Lapins'. The fruit is very firm, very large, has a sweet taste, and is tolerant to rain splitting. The tree is upright to upright spreading in habit, moderately vigorous, self-compatible, precocious and very productive, and has produced good crops annually since fruiting commenced. The variety was named 'Skeena' in 1996. The leaves of 'Skeena' are less glossy than the comparison varieties. The leaves are horizontal in attitude relative to the shoot and have dentate margins. The petioles are long and have 2 or 3 nectaries per petiole. 'Skeena' flowers in the middle of the bloom season and has white, single in type flowers that appear in clusters. The petals of the flowers are broad elliptic in shape and are overlapping.

5 Drawing Sheets

BACKGROUND OF THE INVENTION

Field of Invention

Botanical Description of the Plant

Name: 'Skeena'.
*Genus.*—*Prunus.*
*Species.*—*avium.*
*Market class.*—Sweet Dessert.
*Parentage.*—'2N-60-7'×'2N-38-32'.

Name: '2N-60-7'.
*Genus.*—*Prunus.*
*Species.*—*avium.*
*Marked class.*—For breeding purposes only.
*Parentage.*—'Bing'×'Stella'.

Name: '2N-38-32'.
*Genus.*—*Prunus.*
*Species.*—*avium.*
*Market class.*—For breeding purposes only.
*Parentage.*—'Van×Stella'.

This invention relates to cherry trees and particularly to a seedling cherry tree from a controlled cross made by Dr. W. David Lane of the Pacific Agri-Food Research Centre Summerland cherry breeding program located at Summerland, British Columbia, Canada.

The Agriculture and Agri-Food Canada research facility at Summerland was established in 1914. Originally called the Dominion Experimental Farm at Summerland, the name was changed to the Summerland Research Station in 1959, the Summerland Research Centre in 1994 and to the Pacific Agri-Food Research Centre (PARC) Summerland in 1996. The tree fruit breeding program was established in 1924 to provide new varieties for the tree fruit industry of British Columbia, Canada, and the world. The breeding program at Summerland has produced several tree fruit varieties including 'Spartan' (unpatented), 'Summerred' (unpatented), and 'Sunrise' (unpatented), apples and 'Van' (unpatented), 'Lapins' (unpatented), and 'Sweetheart' (unpatented), sweet cherries. The tree fruit breeders typically produce several thousand seedlings each year.

The three broad objectives of the cherry breeding program are: 1) to diversify the product to allow growers to take advantage of niche markets; 2) to increase environmental adaptation to major fruit growing areas, to insure consistent production of high quality fruit; 3) to reduce the cost of production. The varieties are evaluated for the following traits to insure that the objectives are met. Primary traits include: early onset of bearing, self-compatibility, extended ripening season, fruit size, fruit firmness, and resistance to cracking. Secondary traits include: disease resistance, winter hardiness, resistance to spring frosts, and compact tree growth habit. Upon fruiting, the seedlings are evaluated for fruit and tree quality. Bloom and harvest indices, disease susceptibility and growth habit are evaluated in the field. Promising seedlings are re-propagated, by budding or grafting onto rootstocks, and planted out as first selections in variety evaluation plots. The reproductions are evaluated for varietal stability, disease susceptibility, and fruit and tree quality. The most promising selections are re-propagated again and planted out in randomized evaluation plots complete with reference varieties (commercial varieties). Upon fruiting, selections are evaluated for varietal stability in the field, and for fruit quality in "in-house" sensory evaluation panels. The new varieties are compared to reference varieties to establish uniqueness.

The present invention relates to a new and distinct variety of cherry tree which was named 'Skeena' in 1995. The original cross was made in 1976 by breeder Dr. W. David Lane. The variety is the offspring of the seed parent '2N-60-7' (a 'Bing'×'Stella' cross from the breeding program at Summerland) unpatented and the pollen parent '2N-38-32' (a 'Van'×'Stella' cross also from the Summerland Program)

unpatented. The variety was planted out as a seedling in 1984 and given the Breeder's Reference Number '13S-43-48'.

Distinguishing Characteristics

Under growing conditions at the Pacific Agri-Food Research Centre (PARC) Summerland located at Summerland in the Okanagan Valley of British Columbia, Canada, the variety 'Skeena' consistently has the following characteristics. The variety is a self-compatible, late-season cherry. The fruit matures about 12 to 16 days after 'Van and 'Bing', 1 to 5 days after 'Lapins' and 3 to 7 days before 'Sweetheart'. The fruit of 'Skeena' is kidney shaped with a flat to slightly hollow apex (blossom end) and is borne on medium to long, thick stems. The fruit has wine-red to mahogany colored skin with fine white dots and red to dark red flesh. The fruit is large and firm averaging 11.6 g in weight and a rating of 80 in firmness (as measured by Shores Durometer). It has a good resistance to rain splitting averaging 20% splits over 15 years of trials. The fruit is sweet, averaging about 19% soluble solids and is medium to very juicy. The shape of the stone of 'Skeena' is round in the basal, front and lateral views. The stone of 'Skeena' is large in size and large relative to the size of the fruit.

The leaves of 'Skeena' are less glossy than the comparison varieties and have dentate margins. The leaves are horizontal in attitude relative to the shoot. The petioles are green and long (over 2.5 cm in length) and have 2 or 3 red nectaries per petiole.

'Skeena' flowers in the middle of the bloom season, within one day of 'Van' and 'Bing', and about 2 days after 'Lapins'. The variety is self-compatible. The flowers are white, single in type, and appear in clusters. The petals of the flowers are broad elliptic in shape and are overlapping.

The tree of 'Skeena' is of moderate vigor and hardy to Zone 6A. The habit of 'Skeena' is upright. The tree is very precocious and very productive, and has produced good crops annually since first fruiting. The one-year-old dormant shoots show little or no anthocyanin coloration and are, on average, of medium diameter at the middle of the shoot (about 6 mm). On average the internodes of 'Skeena' are long and have few lenticels. The buds on the one-year-old shoots are ovate and are slightly held out in relation to the shoot.

Parent Plants

'Skeena' is the result of a controlled cross of the seed parent '2N-60-7' (a 'Bing'×'Stella' cross from the breeding program at Summerland) and the pollen parent '2N-38-32' (a 'Van×'Stella' cross also from the Summerland program) made in 1976 at the Pacific Agri-Food Research Centre at Summerland British Columbia, Canada.

'2N-60-7' is the result of a controlled cross of the seed parent 'Bing' and the pollen parent 'Stella' made at the Pacific Agri-Food Research Centre, Summerland in 1965.

'2N-38-32' is the result of a controlled cross of the seed parent 'Van' and the pollen parent 'Stella' made at the Pacific Agri-Food Research Centre, Summerland in 1965.

Neither '2N-60-7' nor '2N-38-32' were of commercial quality and were dropped from the program. The selections were used as parents due to their parent combinations ('Van', 'Bing' and 'Stella' are commercial varieties and 'Stella' has the ability to pass on self-fertility).

Summary of the Invention

The new and distinct variety of *Prunus avium* fruiting cherry tree, 'Skeena', resulted from a controlled cross made in 1976 at the Pacific Agri-Food Research Centre in Summerland, British Columbia, Canada by breeder Dr. W. David Lane. The seedling was established in a selection block in 1980 and given the breeder's reference number '13-S-43-48' in 1984. The variety has been established and is being maintained at the research facility. The variety was first propagated in 1987 by budding on Mazzard F12/1 rootstock and was established in a second selection field at the Pacific Agri-Food Research Centre at Summerland, British Columbia, Canada in 1989. Evaluations began upon fruiting.

The variety is stable with no variations occurring, and demonstrates significant differences from its parents and other fruiting cherry varieties in that the fruit of 'Skeena' matures late in the cherry season, is large and very firm with a flat to hollow apex at the blossom end. The skin of 'Skeena' is wine-red to mahogany in color, glossy ,with fine light-colored highlights. The flesh is red to dark red. The fruit is sweet (19% soluble solids) with little or no astringency and medium acidity (604 titratable units). The fruit is tolerant to rain splitting (20% natural rain splits). The stone of 'Skeena' is large in comparison to the fruit, round and symmetrical in the lateral view and round in the front view. The keel of the stone is undeveloped. The tree habit is upright to upright spreading and of moderate vigor. The tree is self-compatible, very productive and precocious.

BRIEF DESCRIPTION OF THE PHOTOGRAPHS

The accompanying 5 sheets of photographs show various characteristics of the cherry variety 'Skeena'.

FIG. 1 shows a typical dormant tree of 'Skeena' approximately 7 years old. This figure shows the growth habit of the tree.

Figure 2:
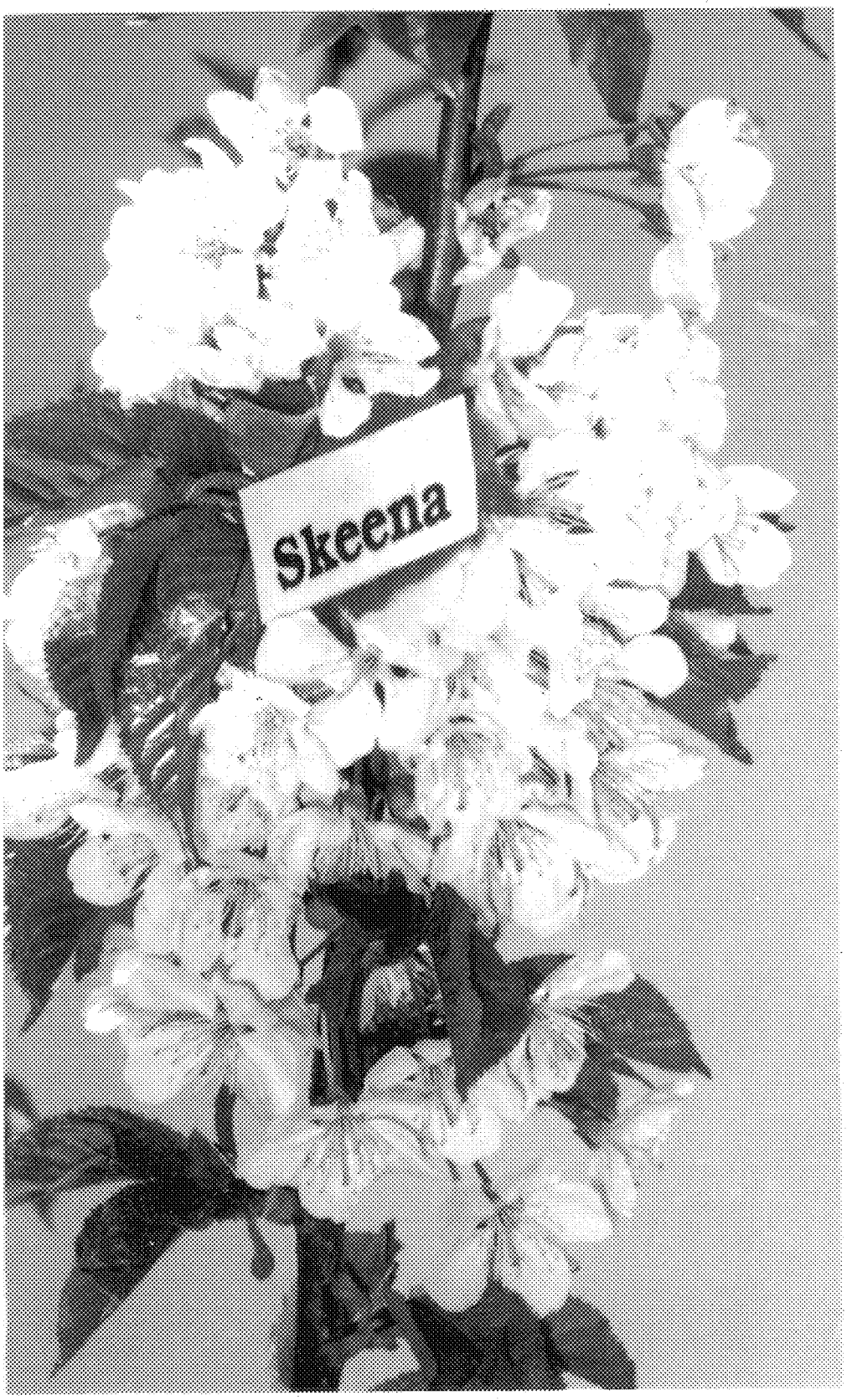

In FIG. 2 a typical branch at blossom is shown. The blossoms are at about full bloom.

Figure 3:
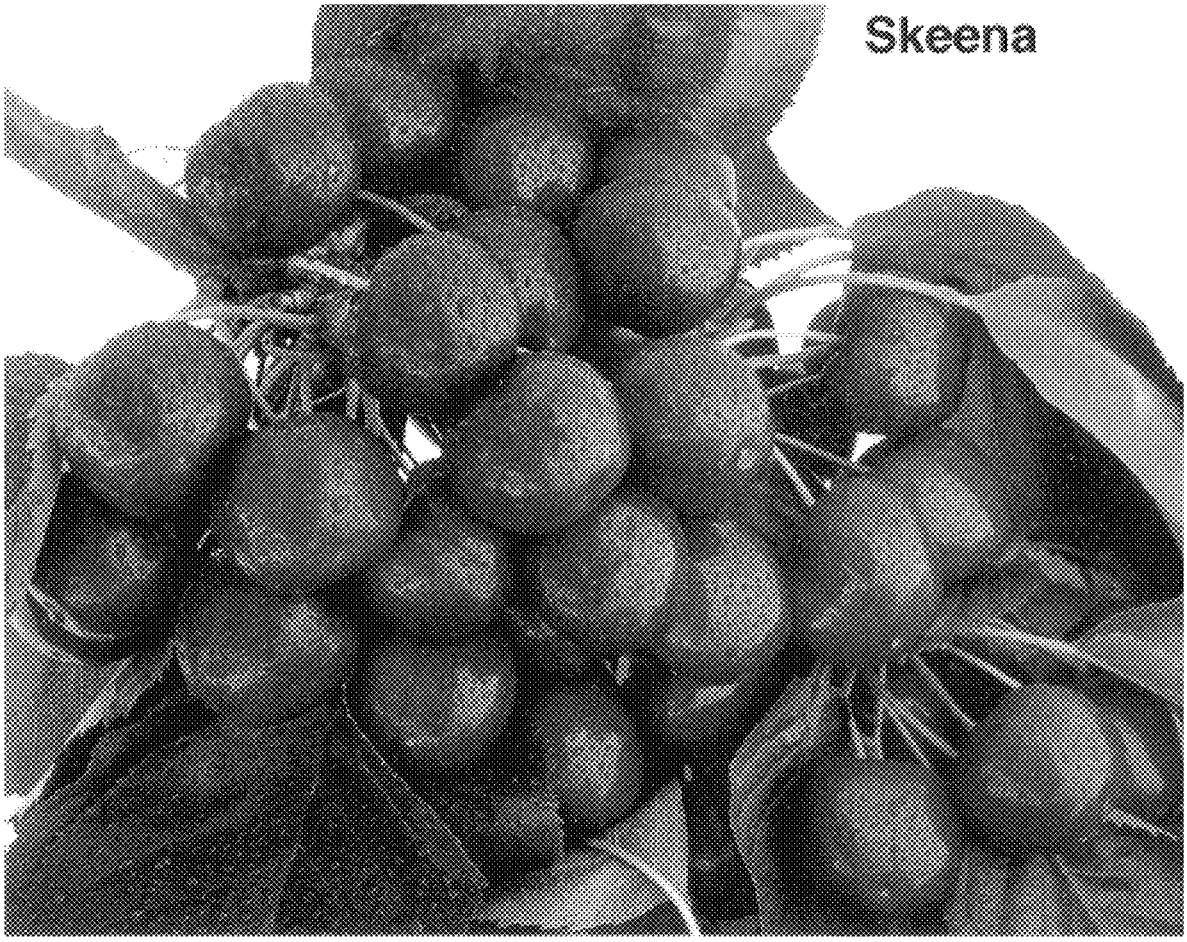

FIG. 3 shows a typical branch with fruit somewhat prior to harvest. This figure illustrates the cluster of fruit, the leaves and the bark color of the variety.

Figure 4:
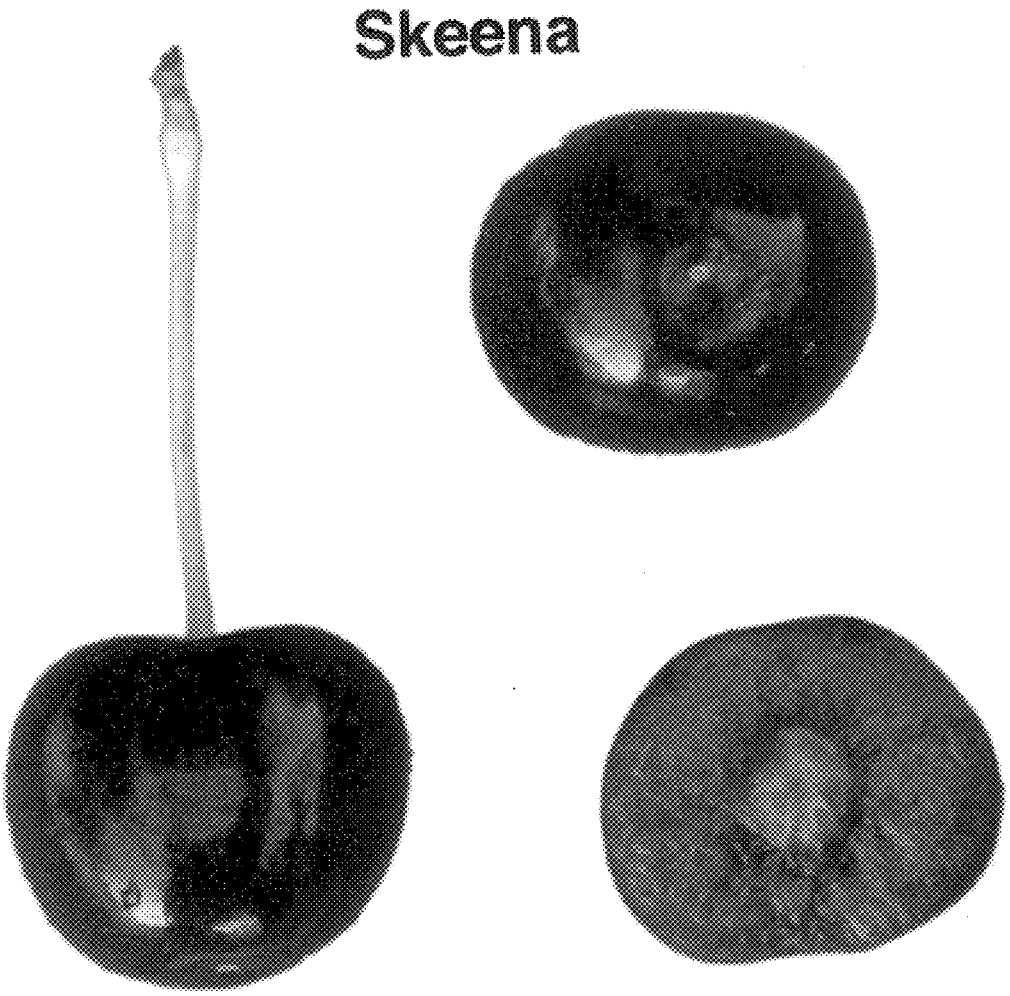

FIG. 4 illustrates the mature fruit of 'Skeena' in large scale. The fruit is arranged to display the blossom end (top right) and the side view (middle left) of the fruit. These views show the color of the fruit at maturity The fruit is displayed in cross section after being cut centrally across the midline (middle right). The flesh color and the arrangement of the flesh in relation to the stone is displayed.

Figure 5:
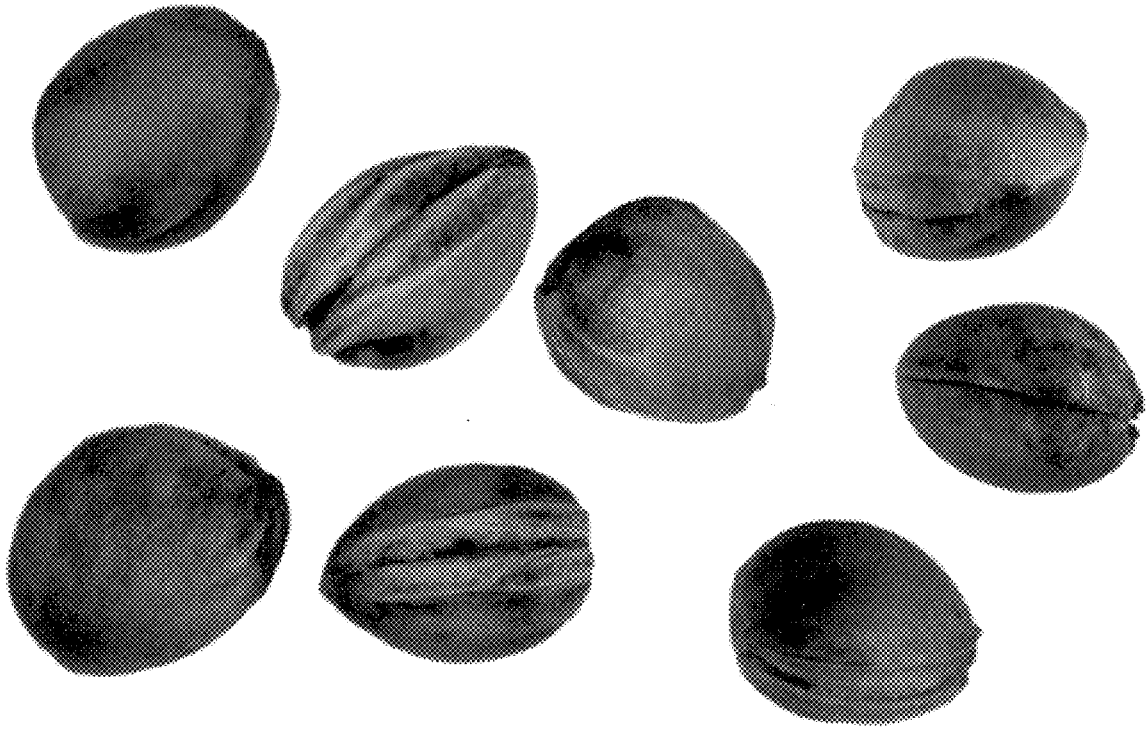

FIG. 5 shows various views of the stone of the fruit after drying and the flesh is removed. The basal, lateral and front views are displayed as well as views showing the undeveloped keel. All colors as set forth in the specification refer to those set forth by The Royal Horticultural Society Colour Chart (R.H.S.). Colors as shown are as close as is possible to attain in a color illustration of this character.

Trials and Evaluations

A seedling resulting from a controlled cross made in 1976 was planted into a seedling block and given the Breeder's Reference Number '13S-43-48' in 1984. '13S-43-48' was reproduced in 1987 and planted in cultivated variety blocks, complete with standards, at the Pacific Agri-Food Research Centre (PARC) Summerland orchards in 1989. The reproductions have shown 'Skeena' ('13S-43-48') to be stable with no variations occurring. The variety has been observed and evaluated since first fruiting.

Test plots established at PARC Summerland consisting of 4 trees of 'Skeena' ('13S-43-48') were established in 1989. The variety was compared to the reference varieties 'Bing', 'Van', and 'Lapins' of approximately the same age and planted in the same area. Controlled grower trials, under test agreements, have been established in British Columbia and in selected sites in the United States.

'Skeena' was evaluated for self-fertility, fruit size, fruit firmness, maturity date, fruit taste (soluble solids and titratable acids), natural rain splits, tree growth habit, fruit shape, productivity, precocity and disease susceptibility and disease resistance, from first fruiting in 1982 until the present.

At Summerland, 'Skeena' has larger average fruit size than 'Van', 'Bing' and 'Lapins'. 'Skeena' has proven to be firmer, on average, than the reference varieties. The variety matures on average, 12 to 16 days later than 'Van' and 'Bing' and 1 to 5 days later than 'Lapins'. 'Van' and 'Bing' mature on average about the first week of July in Summerland. The flesh of 'Skeena' is rated slightly firmer than 'Lapins' and 'Van' and significantly firmer than 'Bing'. The fruit of 'Skeena' on average is as sweet as 'Van' and 'Bing' and sweeter than 'Lapins' and has more titratable acids than 'Van' and 'Lapins' (no measurements were taken for 'Bing'). 'Skeena' is as tolerant to rain spitting as 'Lapins' and much more tolerant to rain splitting than 'Van' or 'Bing'. In laboratory cracking index trials 'Skeena' is as tolerant to splitting as 'Lapins' and much more tolerant than 'Van' (no trials were done on 'Bing'). 'Skeena' has a flat, slightly hollow apex similar to 'Lapins'. 'Bing' and 'Van' have more pointed apices. The stone of 'Skeena' has an undeveloped keel as does 'Lapins'. 'Bing' and 'Van' have medium developed keels. The shape of the stone of 'Skeena' is round in the basal, front and lateral views while 'Lapins', 'Van', and 'Bing' are elliptical from the front view. The stone of 'Skeena' is large in size and is large relative to the fruit.

The leaves of 'Skeena' are less glossy than the comparison varieties and have dentate margins. The margins of 'Lapins' are dentate and 'Van' and 'Bing' have serrate margins. All four varieties have leaves that are elliptic in shape and have an acute angle at the tip. The attitude of the leaves in relation to the shoot of 'Skeena', 'Van', and 'Bing' are horizontal. The petioles of all the varieties are green and large (over 2.5 cm in length). 'Skeena' has 2 to 3 nectaries per petiole, 'Lapins' has 2 nectaries, 'Van' has 2 nectaries and 'Bing' has 1 or 2 nectaries.

'Skeena' flowers in the middle of the bloom season, within one day of 'Van' and 'Bing', and about 2 days after 'Lapins'. The variety is self-compatible as is 'Lapins' while 'Van' and 'Bing' are not. The flowers of all the varieties are white, single in type, and appear in clusters. The petals of the flowers are white and are broad elliptic in shape except 'Van' which has round petals. The petals are overlapping in 'Skeena', partially overlapping in 'Van' and 'Bing', and just touching in 'Lapins'.

The tree of 'Skeena' is of moderate vigor, while 'Lapins' is of moderate to strong vigor and 'Van' and 'Bing' are of moderate vigor. All four varieties are hardy to Zone 6A. The habit of 'Skeena' is upright to upright spreading, 'Van' and 'Bing' are spreading, while 'Lapins' is upright. There is little or no anthocyanin coloration on the one-year-old dormant shoots on any of the varieties. On average the shoots of 'Skeena' and 'Van' are of medium diameter at the middle of the shoot (about 6 mm), while 'Bing' (about 4 mm) and 'Lapins' (about 5 mm) are smaller. On average the internodes of 'Skeena' are longer than the reference varieties and there are few lenticels on the shoots of any of the varieties. The buds on the one year-old-shoots are ovate in all the varieties. In relation to the shoot, the buds of 'Skeena' are slightly held out while, buds of 'Van' and 'Bing' are appressed and 'Lapins' buds are clearly held out.

Virus Status and Disease Susceptibility/Resistance

Wood of Skeena has been virus indexed at the Centre for Plant Health at Sidney B.C. and virus certified trees have been established at the okanagan Plant Improvement Companies Certified Budwood Orchard.

Skeena has shown no unusual susceptibility nor resistance to any plant or fruit pests and/or diseases.

Pomological characteristics: 'Skeena',

Fruit end use: Dessert.

*Group.*—Sweet. Measurements are from trees are of the approximately the same age on Mazzard F12/1 for rootstock.

Growth Characteristics: Observations are measurements from 6 year old bearing trees.

*Tree vigor.*—Moderate.
*Tree height.*—Less than 7 m at 6 years old.
*Tree width.*—Less than 7 m at 6 years old.
*Growth habit.*—Upright to upright spreading.
*Branch pubescence.*—Very slight.
*Bearing.*—Annual and regular.

Shoot characteristics: Measurements are the mean of 10 shoots.

*Shoot attitude.*—Erect.
*Wood bud shape.*—Ovate.
*Position of bud.*—Slightly held out.
*Number of lenticels.*—Few to-medium.
*Shoot diameter.*—Mean: 6 mm (middle of shoot). Range: 2.5 mm.
*Internode length.*—Mean: 47.2 mm (middle of shoot). Range: 29 mm.
*Anthocyanin coloration (Shoot tip).*—Absent or very weak.
*Bark coloration 1st year wood.*—165B (R.H.S.) (at maturity).
*Bark coloration mature branch.*—165A (R.H.S.) (at maturity).
*Bark coloration trunk.*—166A (R.H.S.) (at maturity).

Leaf characteristics: Measurements are the means of 10 leaves.

*Bud burst.*—Mid period as compared to other varieties.
*Attitude to shoot.*—Horizontal.
*Leaf shape.*—Elliptical with broad base.
*Angle at blade tip.*—Acute.
*Shape of base.*—U-shape.
*Shape of apex.*—Cuspidate to acuminate.
*Leaf color upper side.*—147A (R.H.S.).
*Leaf color lower side.*—147B (R.H.S.).
*Anthocyanin (bud burst).*—Present at margins .
*Anthocyanin upper side.*—Absent to weak.
*Anthocyanin (leaf glands).*—Present.
*Glossiness of upper side.*—Weak-medium.
*Margin indentation.*—Dentate.
*Degree of indentation.*—Shallow.
*Leaf length.*—Mean: 150 mm. Range: 3.6 mm.
*Leaf width.*—Mean: 70 mm. Range: 2.1 mm.
*Blade ratio.*—Length/width: 2.1.
*Petiole length.*—Mean: 3.6 cm. Range: 1 mm.
*Petiole/blade.*—Mean: 4.1. Range: 1.3.

*Petiole anthocyanin.*—59A (R.H.S.) On upper half of petiole.
*Number of nectaries* (*out of 10*).—2–4.
*Nectaries color.*—45A (R.H.S.) (on mature leaves).

*Flower characteristics.*—Measurements are the mean of 10 flowers.
*Bloom period.*—Within one day of 'Van' and 'Bing'.
*Flowers per cluster.*—3 to 10 per cluster.
*Duration of bloom.*—5 to 7 days.
*Flowering density.*—Sparse to medium.
*Flower appearance.*—In clusters.
*Flower type.*—Single.
*Flower size.*—Mean: 39.7 mm. Range: 2 mm.
*Pedicel length.*—Mean: 19.3 mm. Range: 2 mm.
*Pedicel thickness.*—Mean: 1.3 mm. Range 0.6 mm.
*Petal size* (*length*).—Mean: 19.3 m. Range: 10 mm.
*Petal shape.*—Broad elliptic.
*Petal position of margins.*—Overlapping.
*Petal color.*—155D (R.H.S.).
*Frequency of supplementary pistil.*—Absent.
*Pistil presence.*—Normal pistil.
*Ovary pubescence.*—Absent.

Fruit characteristics: Measurements are the means from a 10 fruit sample.
*Maturity date.*—About the third week of July at Summerland.
*Weight* (*average*).—Mean: 11.6 g. Range: 1.6 g.
*Large diameter.*—Average about 30 mm.
*Fruit length.*—Average about 26 mm.
*Shape.*—Kidney.
*Symmetry of fruit.*—Symmetrical.
*Position of largest diameter.*—Middle.
*Profile in lateral view.*—Rounded.
*Suture.*—Indistinct.
*Fruit apex.*—Flat to hollow.
*Color of flesh.*—187A (R.H.S.).
*Color of skin.*—187A to 185A (R.H.S.).
*Dots on skin.*—Fine (light color).
*Firmness of flesh.*—80 (Shores Durometer).
*Natural rain splits.*—Slightly susceptible (20%).
*Fruit taste.*—Sweet.
*Juice color.*—187C (R.H.S.) (black red).
*Fruit juiciness.*—Medium to very juicy.
*Soluble solids.*—19.2%.
*Titratable acids.*—604 mg per 100 ml of juice.
*Length of stalk.*—Mean: 3.6 cm . Range: 0.5 mm.
*Stalk thickness.*—Mean: 1.3 mm. Range: 0.31 mm.
*Adherence of flesh to stone.*—Semi-adherent.
*Stone size.*—Mean: 9.4 mm. Range: 2.3 mm.
*Stone size relative to fruit.*—Large.
*Stone shape in lateral view.*—Round.
*Stone shape front view.*—Round.
*Stone shape basal view.*—Round.
*Stone keel.*—Undeveloped.
*Stone color.*—165C.
*Compatibility.*—Self-compatible.
*Fruit set* (*yield efficiency*).—High.
*Storage.*—At least 2 weeks at 0 degrees C. At least 4 weeks in Modified Atmosphere. Packaging.

We claim:

1. A new and distinct variety of cherry tree, substantially as herein illustrated and described, named 'Skeena', originating from a controlled cross of the seed parent '2N-60-7' and the pollen parent '2N-38-32' and distinguished from other varieties in that the fruit that is kidney shaped with a flat to slightly hollow apex, matures late in the cherry harvest season (about 12 to 16 days after 'Van' and 'Bing'), has glossy, wine red to mahogany colored skin with fine light-colored highlights and red to dark red flesh, is very large, very firm, sweet, rain tolerant, and has a large round stone with an undeveloped keel, is borne on medium to long, thick stems and is produced on a tree that is moderately vigorous, upright to upright spreading in habit, is precocious and very productive, produces good crops annually, and is self-compatible and has leaves that are oriented horizontally to the shoot with petioles with 2 or 3 nectaries and that flowers in the middle of the bloom season producing single type flowers in clusters that have medium sized, broad elliptic shaped, overlapping petals, under growing conditions at Summerland in the Okanagan Valley of British Columbia, Canada.

* * * * *